(12) United States Patent
Epstein

(10) Patent No.: US 12,094,570 B2
(45) Date of Patent: Sep. 17, 2024

(54) MACHINE LEARNING CHARACTERIZATION OF SPERM QUALITY FOR SPERM SELECTION FOR ASSISTED REPRODUCTION TECHNOLOGY

(71) Applicant: David Charles Epstein, San Mateo, CA (US)

(72) Inventor: David Charles Epstein, San Mateo, CA (US)

(73) Assignee: David Charles Epstein, San Mateo, CA (US)

( * ) Notice: Subject to any disclaimer, the term of this patent is extended or adjusted under 35 U.S.C. 154(b) by 0 days.

(21) Appl. No.: 18/048,564

(22) Filed: Oct. 21, 2022

(65) Prior Publication Data
US 2024/0136012 A1    Apr. 25, 2024
US 2024/0233864 A9    Jul. 11, 2024

(51) Int. Cl.
*G06T 7/00*      (2017.01)
*G06T 11/00*    (2006.01)
(Continued)

(52) U.S. Cl.
CPC ............ *G16B 20/00* (2019.02); *G06T 7/0012* (2013.01); *G06T 11/00* (2013.01); *G16B 40/20* (2019.02);
(Continued)

(58) Field of Classification Search
CPC ...... G16B 20/00; G16B 40/20; G06T 7/0012; G06T 11/00; G06T 2200/24;
(Continued)

(56) References Cited

U.S. PATENT DOCUMENTS 5,763,206 A * 6/1998 Hammerstedt ...... G01N 33/689
                                                          424/581
11,481,900 B2 * 10/2022 Singh ..................... G06T 7/246
(Continued)

OTHER PUBLICATIONS

De Angelis et al. "A Combined Holographic and Raman Microscopy Approach for the Assessment of Spermatozoa." Fotonica AEIT Italian Conference on Photonics Technologies, May 6, 2015, 4 pages (Year: 2015).*

(Continued)

*Primary Examiner* — Jon Chang
(74) *Attorney, Agent, or Firm* — Alston & Bird LLP

(57) ABSTRACT

A user computing entity provides a specimen score for use in selecting a sperm for use in a fertilization event. The user computing entity provides the score by obtaining specimen image data comprising imaging data of one or more specimen, the imaging data corresponds to at least one type of imaging; generating a specimen scoring request including the specimen image data; providing the specimen scoring request for receipt by a network computing entity; receiving a specimen response comprising a respective specimen score for the one or more specimen, the respective specimen score for the one or more specimen generated by a machine-learning trained specimen analysis model; processing the respective specimen score for the one or more specimen to generate a graphical representation of the respective specimen score; and causing display of the graphical representation of the respective specimen score.

20 Claims, 6 Drawing Sheets

(51) Int. Cl.
 G16B 20/00 (2019.01)
 G16B 40/20 (2019.01)
(52) U.S. Cl.
 CPC .............................. G06T 2200/24 (2013.01); G06T 2207/10056 (2013.01); G06T 2207/20081 (2013.01); G06T 2207/30004 (2013.01)
(58) Field of Classification Search
 CPC . G06T 2207/10056; G06T 2207/20081; G06T 2207/30004
 See application file for complete search history.

(56) References Cited

U.S. PATENT DOCUMENTS

| 2021/0158521 | A1* | 5/2021 | Shaked | G06T 7/13 |
| 2021/0374952 | A1* | 12/2021 | Shafiee | G01N 15/1429 |
| 2023/0061402 | A1* | 3/2023 | Cassuto | G06T 7/0014 |

OTHER PUBLICATIONS

World Health Organization. "WHO Laboratory Manual for the Examination and Processing of Human Semen", 2010, 286 pages (Year: 2010).*
De Angelis et al. "Advanced Label-Free Optical Methods for Spermatozoa Quality Assessment and Selection." IntechOpen, Spermatozoa—Facts and Perspectives (Meccariello et al., ed.), DOI: 10.5772/intechopen.71028, Dec. 20, 2017, pp. 219-240 (Year: 2017).*
American Society for Reproductive Medicine, "Optimizing natural fertility: a committee opinion", ASRM Pages, Fertility and Sterility, 117(1):53-63, (Jan. 2022).
Ankit Butola et al., "High spatially sensitive quantitative phase imaging assisted with deep neural network for classification of human spermatozoa under stressed condition", Scientific Reports, 10:1-12, (2020).
Ashok Agarwal et al., "A unique view on male infertility around the globe", Reproductive Biology and Endocrinology, 13:1-9, (2015).
C. Mallidis et al., "In situ visualization of damaged DNA in human sperm by Raman microspectroscopy", Human Reproduction, 26(7):1641-1649, (2011).
Christopher Mccallum et al., "Deep learning-based selection of human sperm with high DNA integrity", Communications Biology, https://doi.org/10.1038/s42003-019-0491-6, 2:1-10, (2019).
F. Bronet et al., "Sperm DNA fragmentation index does not correlate with the sperm or embryo aneuploidy rate in recurrent miscarriage or implantation failure patients", Human Reproduction, 27(7):1922-1929, (2012).
Feng Liu et al., "Real-time Raman microspectroscopy scanning of the single live sperm bound to human zona pellucida", Fertility and Sterility, 99(3):684-689, 689.e1-689.e4, (Mar. 1, 2013).
Georgina Avalos-Durán et al., "Physiological ICSI (PICSI) vs. conventionsal ICSI in couples with male factor: A systematic review", JBRA Assisted Reproduction, 22(2):139-147, (2018).
Georgina M. Chambers et al., "The economic impact of assisted reproductive technology: a review of selected developed countries", Fertility and Sterility, 91(6):2281-2294, (Jun. 2009).
Giuseppe Lo Monte et al., "Focus on intracytoplasmic morphologically selected sperm injection (IMSI): a mini-review", Asian Journal of Andrology, 15:608-615, (2013).
H. Oldenhof et al., "Fourier transform infrared spectroscopic analysis of sperm chromatin structure and DNA stability", Andrology, 4:430-441, (2016).
Jae Bem You et al., "Machine learning for sperm selection", Nature Reviews Urology, 18:387-403, (Jul. 2021).
John A. Collins et al., "Do sperm DNA integrity tests predict pregnancy with in vitro fertilization?", Fertility and Sterility, 89(4):823-831, (Apr. 2008).
Konrad Meister et al., "Confocal Raman microspectroscopy as an analytical tool to assess the mitochondrial status in human spermatozoa", Analyst, 135:1370-1374, (2010).
Lodovico Parmegiani et al., "Comparison of two ready-to-use systems designed for sperm-hyaluronic acid binding selection before intracytoplasmic sperm injection: PICSI vs. Sperm Slow: a prospective, randomized trial", Fertility and Sterility, 98(3):632-637, (Sep. 2012).
M. Y. Jahmani et al., "Label-Free Evaluation of Chromatin Condensation in Human Normal Morphology Sperm Using Raman Spectroscopy", Reproductive Sciences, 28(9):2527-2539 (2021).
Maria Antonietta Ferrara et al., "Label-Free Imaging and Biochemical Characterization of Bovine Sperm Cells", Biosensors, 5:141-157 (2015).
Mathew J. Tomlinson et al., "CASA in the medical laboratory: CASA in diagnostic andrology and assisted conception", Reproduction, Fertility and Development, 30(6):850-859, (2018).
Mengge Li et al., "Evaluation of Laser Confocal Raman Spectroscopy as a Non-Invasive Method for Detecting Sperm DNA Contents", Frontiers in Physiology, 13, Article 827941, (2022).
Mustafa Ugur Daloglu et al., "Label-free 3D computational imaging of spermatozoon locomotion, head spin and flagellum beating over a large volume", Light: Science & Applications, 7:1-11, (2018).
Ning Li et al., "Confocal Raman micro-spectroscopy for rapid and label-free detection of maleic acid-induced variations in human sperm", Biomedical Optics Express, 5(5):1690-1699, (2014).
Peter N. Schlegel et al., "Diagnosis and Treatment of Infertility in Men: AUA/ASRM Guideline", American Urological Association Education and Research, Inc., 1-53, (Oct. 2020).
Pinar Ozcan et al., "Does the use of microfluidic sperm sorting for the sperm selection improve in vitro fertilization success rates in male factor infertility?", The Journal of Obstetrics and Gynaecology Research, 1-7, (2020).
Raul Da Costa et al., "Spectral features of nuclear DNA in human sperm assessed by Raman Microspectroscopy: Effects of UV-irradiation and hydration", PLoS One, https://doi.org/10.1371/journal.pone.0207786, 13(11):1-15, (Nov. 20, 2018).
Rupert P. Amann et al., "Computer-assisted sperm analysis (CASA): capabilities and potential developments", Theriogenology, 81(1):5-17, 17.e1-17.e3, (2014).
Sheree L. Boulet et al., "Trends in use of and reproductive outcomes associated with intracytoplasmic sperm injection", JAMA, 313(3):255-263, (Jan. 20, 2015).
Summer G. Goodson et al., "CASAnova: a multiclass support vector machine model for the classification of human sperm motility patterns", Biology of Reproduction, 97(5):698-708, (2017).
Teixeira DM et al., "Regular (ICSI) versus ultra-high magnification (IMSI) sperm selection for assisted reproduction", Cochrane Database of Systematic Reviews, Issue 2, Article No. CD010167, 46 pages, (2020).
Thomas Huser et al., "Raman spectroscopy of DNA packaging in individual human sperm cells distinguishes normal from abnormal cells", Journal of Biophotonics, 2(5):322-332, (2009).
Thinus F. Kruger et al., "A new computerized method of reading sperm morphology (strict criteria) is as efficient as technician reading", Fertility and Sterility, 59(1):202-209, (Jan. 1993).
Thinus F. Kruger et al., "A prospective study on the predictive value of normal sperm morphology as evaluated by computer (IVOS*)", Fertility and Sterility, 66(2):285-291, (Aug. 1996).
Victoria Sánchez et al., "Oxidative DNA damage in human sperm can be detected by Raman microspectroscopy", Fertility and Sterility, 98(5):1124-1129, 1129.e1-1129.e3, (Nov. 2012).
William L. Kubasek et al., "Raman Spectra of the Model B-DNA Oligomer d(CGCGAATTCGCG)$_2$ and of the DNA in Living Salmon Sperm Show That Both Have Very Similar B-Type Conformations", Biochemistry, 25(23):7440-7445, (1986).
Zhan-Sen Huang et al., "Antioxidative Protective Effect of Icariin on the FeSO$_4$/H$_2$O$_2$-damaged Human Sperm Based on Confocal Raman Micro-spectroscopy", J Huazhong Univ Sci Technol [Med Sci], 34(5):755-760, (2014).

* cited by examiner

MACHINE LEARNING CHARACTERIZATION OF SPERM QUALITY FOR SPERM SELECTION FOR ASSISTED REPRODUCTION TECHNOLOGY

FIELD

Various embodiments relate generally to machine learning-based characterization of sperm quality. For example, various embodiments relate to using a machine learning-trained model for characterizing sperm quality for sperm selection for assisted reproduction technology.

BACKGROUND

According to the American Society for Reproductive Medicine, infertility affects about 15% of couples. The use of assisted reproductive technologies is increasing by 5-10% per year in the United States. Among couples with infertility, male factor accounts for 50% of the cases. Among assisted reproductive technology cycles with male factor infertility, 90% use intracytoplasmic sperm injection (ICSI) for the method of fertilization. The current standard of care involves an embryologist using a light microscopy at low magnification to visually assess morphology and motility to select the most competent sperm. With current selection methods, rates of fertilization and embryo development are low, with a large attrition rate from oocytes to viable embryos available for transfer.

One of the first attempts to automate sperm analysis was computer-assisted sperm analysis (CASA), introduced in the 1980s. CASA systems are automated software to use cameras and analyze data obtained by the microscope. They are useful in analyzing a high number of samples in a short time. They can assess overall sperm quality of a sample (count, motility, path velocity, curvilinear velocity, amplitude of head displacement, and beat cross frequency) but lacks the ability to provide useful assessment at an individual sperm level. Several machine learning algorithms were trained using these CASA parameters to classify sperm by level of motility. CASA also has some inaccuracy in predicting sperm morphology since the shape can change with the plane where the sperm is analyzed. Thus, these conventional sperm analysis techniques have not been found to substantially improve clinical pregnancy rates.

BRIEF SUMMARY OF SOME EXAMPLE EMBODIMENTS

Various embodiments provide methods, apparatuses, computer program products, systems, and/or the like for generating/determining and providing specimen scores for individual specimen. In various embodiments, an individual specimen is an individual sperm. In various embodiments, the specimen scores are generated and/or determined by a machine learning-trained specimen analysis model. In various embodiments, the specimen analysis model is trained to receive specimen image data comprising specimen imaging data of one or more specimen and, optionally, source information for the one or more specimen as input. The specimen analysis model is trained to process the specimen image data and any provided source information and generate and/or determine respective specimen scores for the one or more specimen based thereon.

In various embodiments, a graphical and/or visual representation of the specimen score(s) are displayed via an interactive user interface (IUI) displayed via a display of a user interface. A technician and/or medical service provider may then select to use or not use individual specimen of the one or more specimen to perform respective fertilization events.

According to a first aspect a computer-implemented method for providing a graphical representation of a specimen score for use in selecting a sperm for use in a fertilization event is provided. In an example embodiment, the method includes obtaining, by a user computing entity, specimen image data comprising imaging data of one or more specimen, the imaging data corresponding to at least one type of imaging; generating, by the user computing entity, a specimen scoring request comprising at least a portion of the specimen image data; providing, by the user computing entity, the specimen scoring request for receipt by at least one network computing entity; receiving, by the user computing entity, a specimen response comprising a respective specimen score for each of the one or more specimen, the respective specimen score for each of the one or more specimen generated by a machine-learning trained specimen analysis model executed by the at least one network computing entity, the specimen response provided by the at least one network computing entity; processing, by the user computing entity, the respective specimen score for at least one of the one or more specimen to generate a graphical representation of the respective specimen score; and causing, by the user computing entity, display of the graphical representation of the respective specimen score.

According to another aspect, a user computing entity configured to provide a graphical representation of a specimen score for use in selecting a sperm for use in a fertilization event is provided. In an example embodiment, user computing entity comprises at least one processor and a memory storing computer-executable instructions. The computer-executable instructions are configured to, when executed by the at least one processor, cause the user computing entity to perform the steps of obtaining specimen image data comprising imaging data of one or more specimen, the imaging data corresponding to at least one type of imaging; generating a specimen scoring request comprising at least a portion of the specimen image data; providing the specimen scoring request for receipt by at least one network computing entity; receiving a specimen response comprising a respective specimen score for each of the one or more specimen, the respective specimen score for each of the one or more specimen generated by a machine-learning trained specimen analysis model executed by the at least one network computing entity, the specimen response provided by the at least one network computing entity; processing the respective specimen score for at least one of the one or more specimen to generate a graphical representation of the respective specimen score; and causing display of the graphical representation of the respective specimen score.

According to still another aspect, a computer program product is provided. In an example embodiment, the computer program product comprises a non-transitory computer-readable medium storing computer-executable instructions. The computer-executable instructions are configured to, when executed by one or more processors of an apparatus, cause the apparatus to obtain specimen image data comprising imaging data of one or more specimen, the imaging data corresponding to at least one type of imaging; generate a specimen scoring request comprising at least a portion of the specimen image data; provide the specimen scoring request for receipt by at least one network computing entity; receive a specimen response comprising a respective specimen score for each of the one or more specimen, the respective specimen score for each of the one or more specimen generated by a machine-learning trained specimen analysis model executed by the at least one network computing entity, the specimen response provided by the at least one network computing entity; process the respective specimen score for at least one of the one or more specimen to generate a graphical representation of the respective specimen score; and cause display of the graphical representation of the respective specimen score.

According to yet another aspect, a computer-implemented method for generating and providing a specimen score is provided. In an example embodiment, the method comprises receiving a specimen scoring request, the specimen scoring request comprising specimen image data comprising imaging data of one or more specimen, the imaging data corresponding to at least one type of imaging; executing a machine-learning trained specimen analysis model to process at least a portion of the specimen imaging data to generate a respective specimen score for at least one of the one or more specimen; and providing a specimen response comprising the respective specimen score for receipt by a user computing entity.

According to another aspect, a network computing entity configured to generate and provide a specimen score is provided. In an example embodiment, network computing entity comprises at least one processor and a memory storing computer-executable instructions. The computer-executable instructions are configured to, when executed by the at least one processor, cause the network computing entity to perform the steps of receiving a specimen scoring request, the specimen scoring request comprising specimen image data comprising imaging data of one or more specimen, the imaging data corresponding to at least one type of imaging; executing a machine-learning trained specimen analysis model to process at least a portion of the specimen imaging data to generate a respective specimen score for at least one of the one or more specimen; and providing a specimen response comprising the respective specimen score for receipt by a user computing entity.

According to still another aspect, a computer program product is provided. In an example embodiment, the computer program product comprises a non-transitory computer-readable medium storing computer-executable instructions. The computer-executable instructions are configured to, when executed by one or more processors of an apparatus, cause the apparatus to receive a specimen scoring request, the specimen scoring request comprising specimen image data comprising imaging data of one or more specimen, the imaging data corresponding to at least one type of imaging; execute a machine-learning trained specimen analysis model to process at least a portion of the specimen imaging data to generate a respective specimen score for at least one of the one or more specimen; and provide a specimen response comprising the respective specimen score for receipt by a user computing entity.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 2:
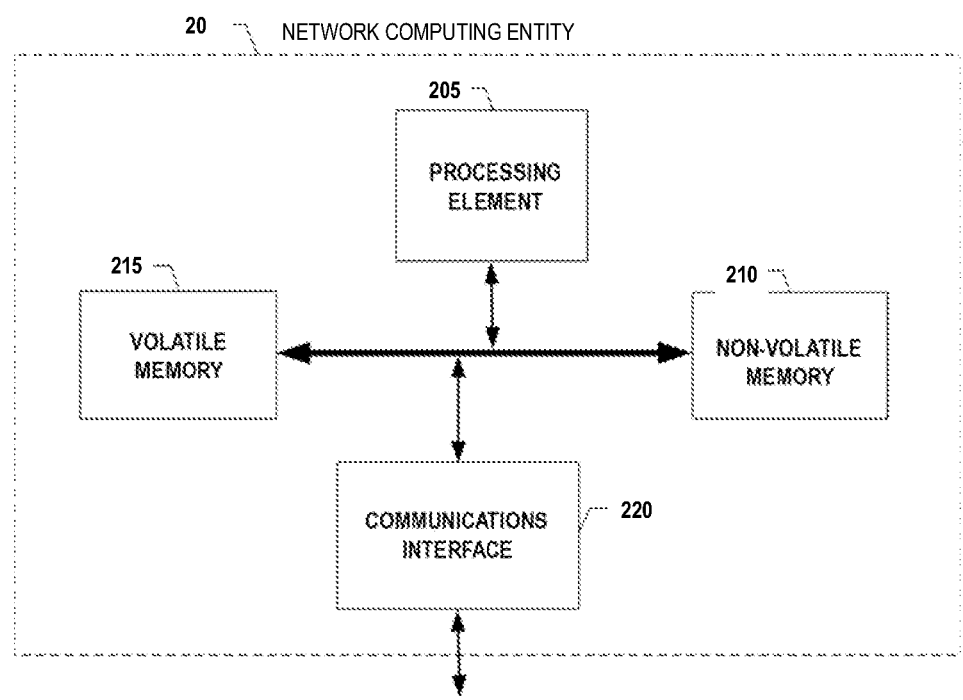
FIG. 2 is a schematic of a network computing entity, in accordance with certain embodiments.
Figure 3:
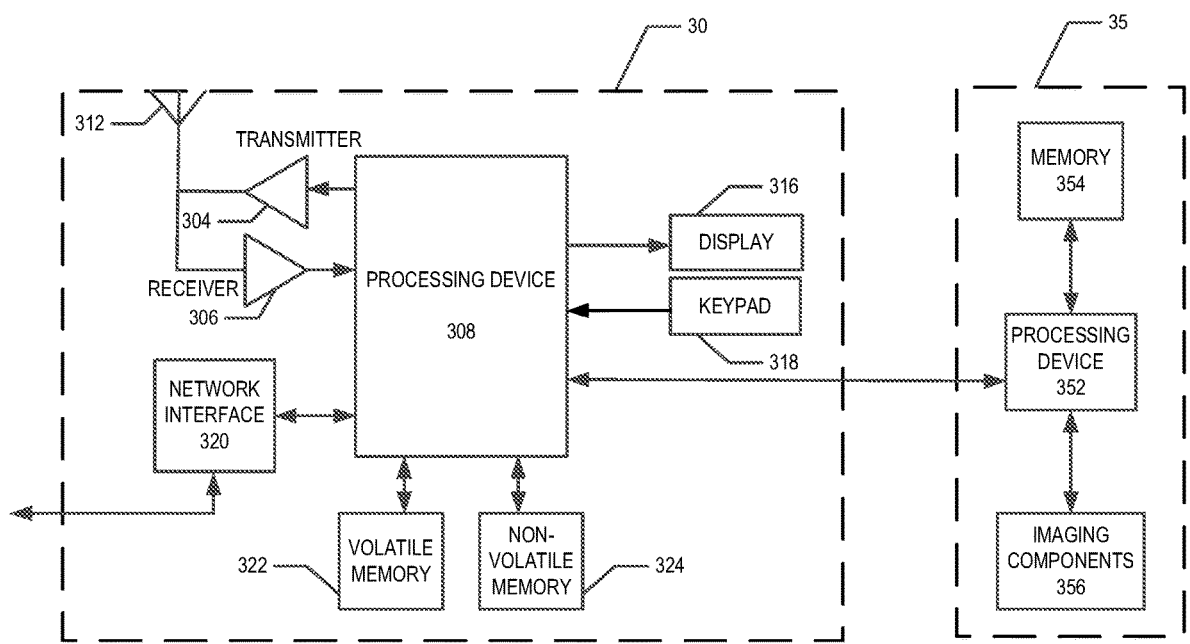
FIG. 3 is a schematic of a user computing entity coupled to an imaging apparatus, in accordance with certain embodiments.
Figure 4A:
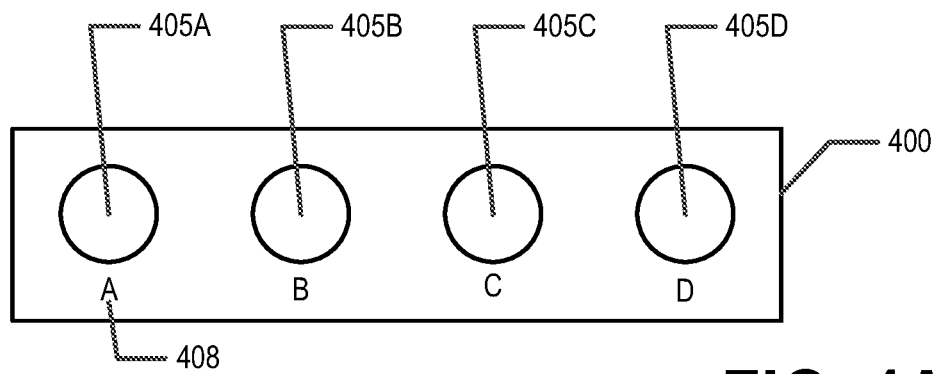
Figure 4B:
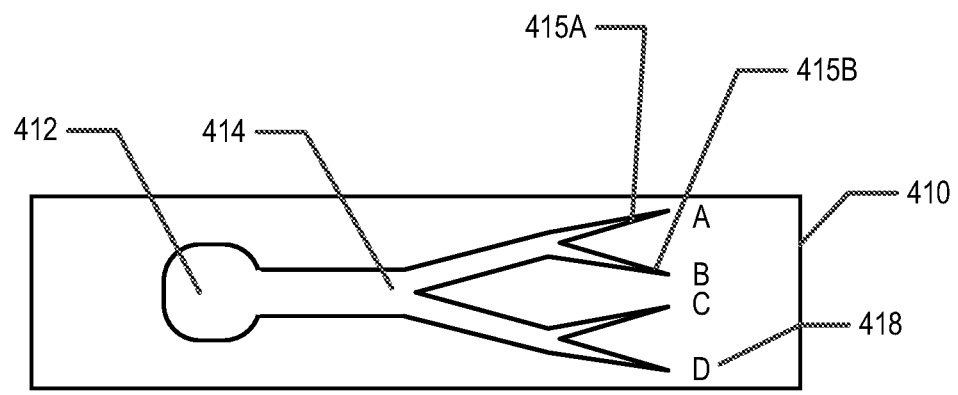
Figure 5:
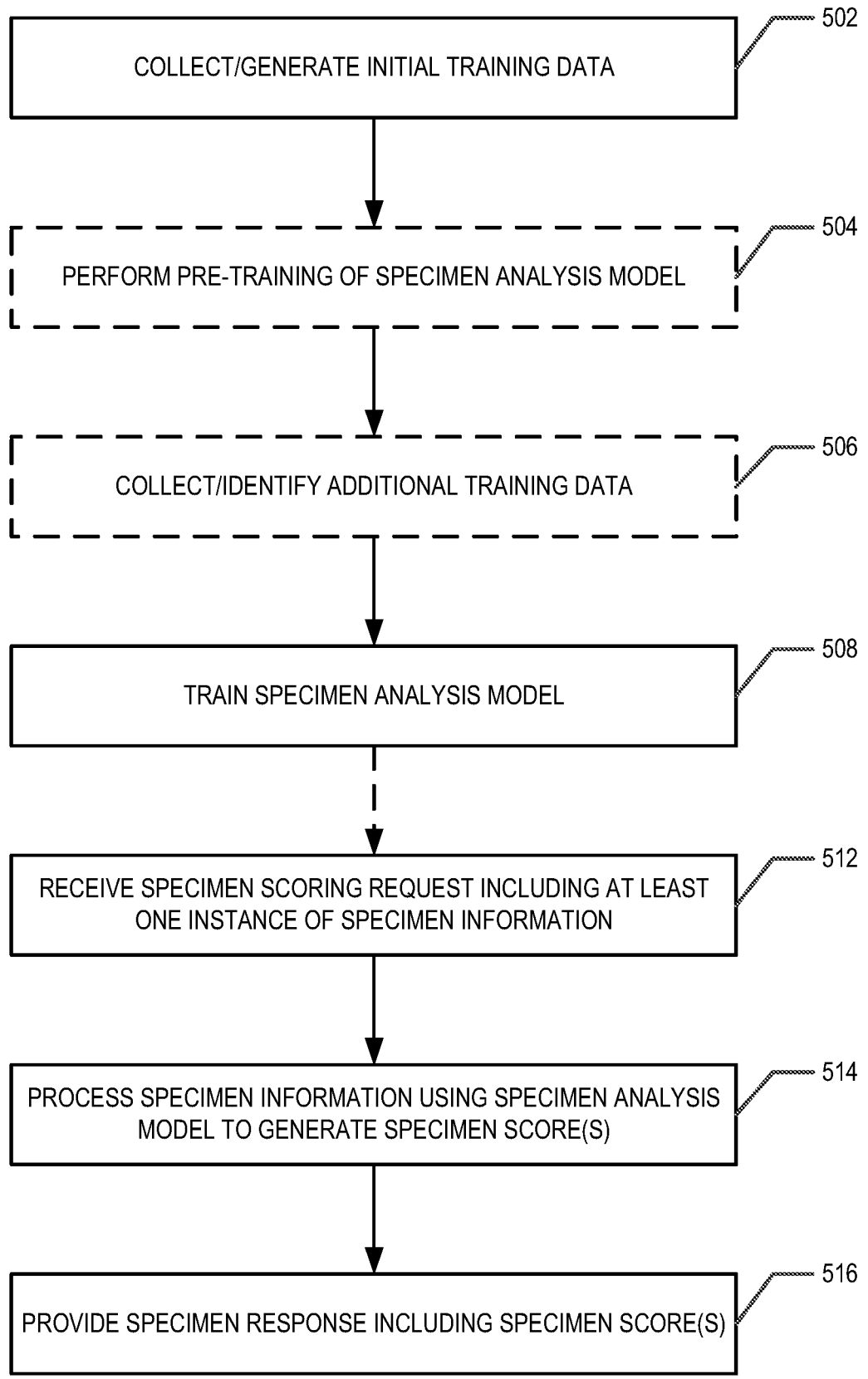
Figure 6:
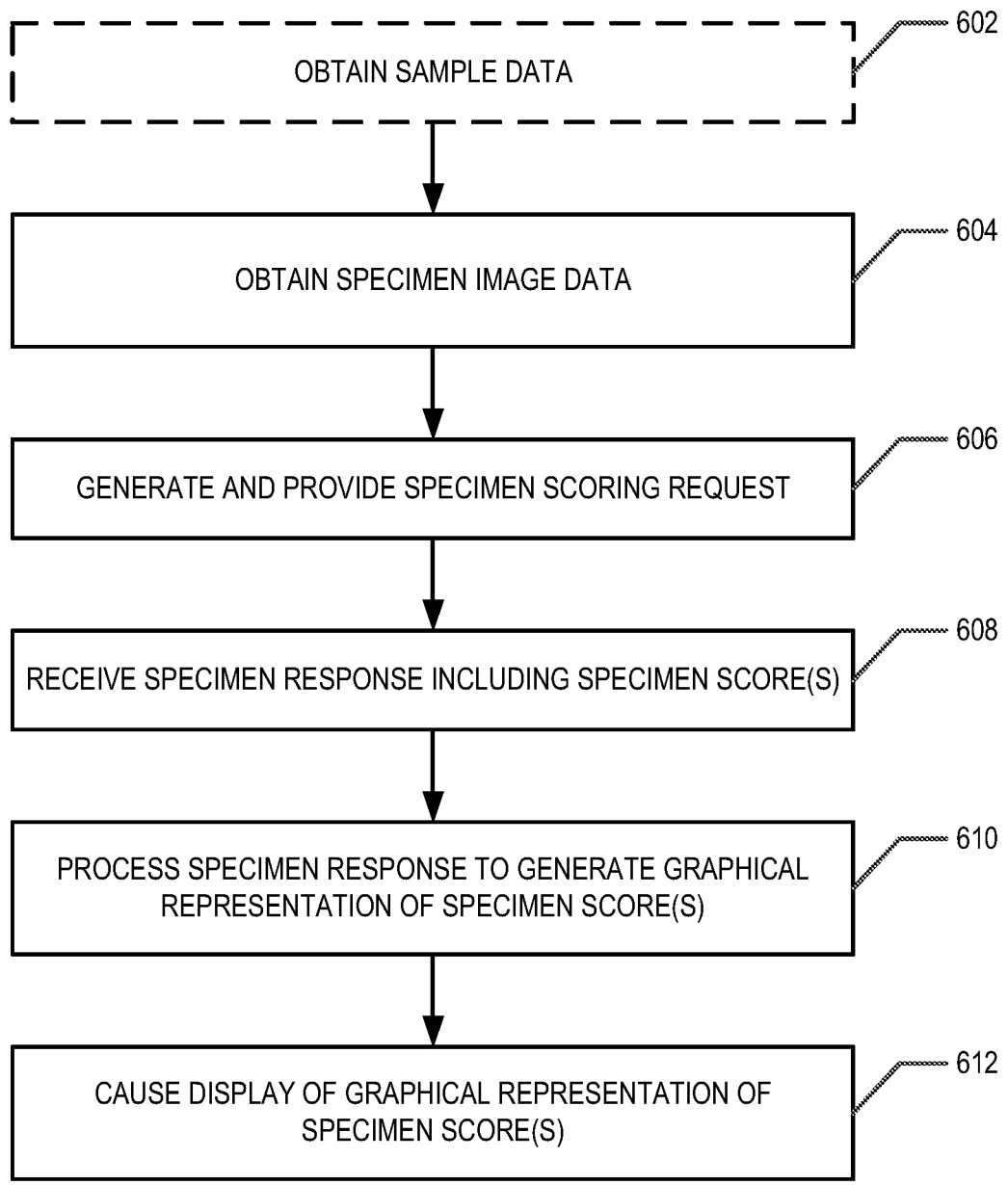

FIGS. 4A and 4B each provide a top view of a respective example slide used for capturing specimen image data, in accordance with certain embodiments;

FIG. 5 provides a flowchart illustrating various processes, procedures, and/or operations performed by a network computing entity of FIG. 2, for example, to train a specimen analysis model and use the specimen analysis model to generate and/or determine specimen scores, in accordance with certain embodiments; and FIG. 6 provides a flowchart illustrating various processes, procedures, and/or operations performed by a user computing entity of FIG. 3, for example, to provide specimen scores, in accordance with certain embodiments.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. General Overview

Various embodiments provide methods, apparatuses, computer program products, systems, and/or the like for generating/determining and providing specimen scores for individual specimen. The terms specimen and sperm are used interchangeably herein. In various embodiments, the specimen scores are generated and/or determined by a machine learning-trained specimen analysis model. In various embodiments, the specimen analysis model is trained to receive specimen image data comprising specimen imaging data of one or more specimen and, optionally, source information for the one or more specimen as input. The specimen analysis model is trained to process the specimen image data and any provided source information and generate and/or determine respective specimen scores for the one or more specimen based thereon.

In various embodiments, a graphical and/or visual representation of the specimen score(s) are displayed via an interactive user interface (IUI) displayed via a display of a user interface. A technician and/or medical service provider may then select to use or not use individual specimen of the one or more specimen to perform respective fertilization events.

In various embodiments, the specimen analysis model is trained using training image data labeled with information corresponding to at least one of successful fertilization, embryo development, or live birth outcomes of a corresponding specimen shown in the training image data. For example, the specimen analysis model is trained to identify characteristics of specimen (e.g., individual sperm) that indicate the specimen is likely to achieve successful fertilization, healthy embryo development, and/or a successful live birth outcome when the specimen is used to perform a fertilization event.

Conventional attempts to automate sperm analysis tend to be based on CASA, introduced in the 1980s. However, CASA can be inaccurate in predicting sperm morphology since the shape of the sperm can change with the plane where the sperm is analyzed. Several machine learning algorithms have been developed using 100× magnified brightfield images of sperm to classify sperm morphology by the World Health Organization (WHO) strict criteria. An example of which, FERTECH software, correlated with technicians reading of sperm morphology 84% of the time. Another system called Integrated Visual Optimal System (IVOS) can automatically analyze an entire sperm-smeared slide but involves sperm staining. These methods are limited by small sample sizes, variable image resolution, and poor reproducibility.

Other conventional methods to improve sperm selection include various sperm filtering techniques such as ZyMot®ICSI chip processing, physiological intracytoplasmic sperm injection (PICSI) and intracytoplasmic morphologically selected sperm injection (IMSI). However, the ZyMot®ICSI microfluidic device was compared to standard preparation for IVF and was not found to improve clinical pregnancy rates. PICSI is a technique using hyaluronic acid coated dished to bind and thus select the "best" functional sperm for ICSI. Some data suggests the bound sperm have lower DNA fragmentation but large randomized control trials have failed to show any significant difference in fertilization and live birth rates over manual sperm selection techniques. IMSI was developed to identify ultrastructural defects in sperm at x6600 magnification but is extremely time consuming for embryologists, taking twice the time as ICSI. Several studies have shown no significant difference in pregnancy outcomes in IMSI vs. ICSI groups.

Raman spectroscopy could be an ideal technique for noninvasive, real-time evaluation of chromosomally and structurally normal sperm to improve fertilization rates and eventually pregnancy rates. The first attempt to analyze sperm with Raman was in Salmon in 1986. Since then, several groups have attempted to use Raman spectroscopy to predict competent sperm based on DNA integrity, mitochondria packaging, and morphology. In the area of Raman and DNA integrity, De Costa et al. and Mallidis et al. detected differences in spectra between UV damaged sperm and controls using principal component analysis (PCA). Another group analyzed Raman, Fourier-transform infrared spectroscopy, and flow cytometry of sperm after oxidative damage. Another study damaged sperm with maleic acid and also detected significant changes in Raman spectra. Research into Raman and chromatin function showed Raman imaging of DNA packaging in abnormally shaped sperm had different Raman findings compared to normally shaped sperm. Another recent study stained for chromatin A3 levels and found significant different spectral analysis among sperm with high and low CMA3 levels. However, all of these studies used fixation techniques for the sperm and some induced DNA damage which in both cases rendered the selected sperm unusable.

Thus, a technical problem exists regarding how to effectively identify sperm that are likely to achieve successful fertilization, healthy embryo development, and/or a successful live birth outcome when the specimen is used to perform a fertilization event without rendering the individual sperm unusable. For example, conventional techniques either do not appear to provide any significant advantage over manual sperm selection techniques or render the individual sperm unusable.

Various embodiments disclosed herein provide technical solutions to these technical problems. In particular, various embodiments use specimen image data corresponding to at least one of vibrational microspectroscopy or quantitative phase imaging (QPI). For example, specimen imaging data of one or more specimen is captured using at least one of vibrational microspectroscopy or QPI techniques. These imaging techniques do not damage the specimen but provide sufficient information for the specimen analysis model to differentiate between individual specimen that are likely to result in successful outcomes versus individual specimen that are less likely or not likely to result in successful outcomes when used to perform a fertilization event. Thus, various embodiments provide specimen scores that provide for improved outcomes of fertilization events when sperm are selected for performance of the fertilization events using the specimen scores compared to conventional methods. Moreover, the specimen imaging data capturing process(es) and the specimen score determination and provision time frame do not render the individual specimen unusable. Thus, the specimen scores can be used to directly select individual specimen in real time (or near real time) for performance of fertilization events. Thus, various embodiments provide improvements to the technical fields of sperm analysis and selection of sperm for performing fertilization events.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

Figure 1:
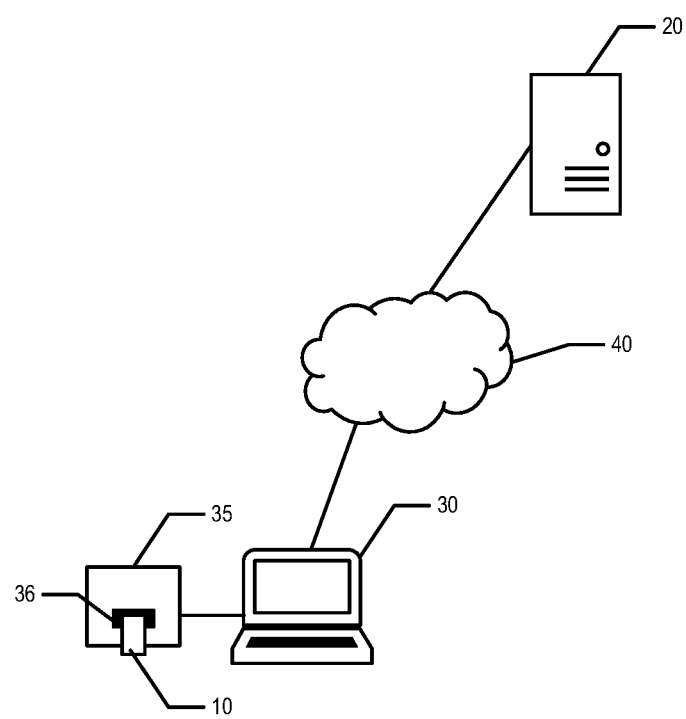
FIG. 1 is a diagram of a system that can be used to practice various embodiments.

FIG. 1 provides an illustration of a system that can be used in conjunction with various embodiments of the present invention. As shown in FIG. 1, the system may comprise one or more network computing entities 20. In various embodiments, a network computing entity 20 is a server, part of a Cloud computing system (e.g., a cloud-based server), a node of a distributed network (e.g., storing a distributed ledger such as a blockchain and/or the like), and/or the like.

As shown in FIG. 1, the system may further comprise one or more user computing entities 30, one or more networks 40, and/or the like. In various embodiments, a user computing entity is a desktop computer, a client device of a network computing entity 20, a laptop, tablet, smartphone, and/or other computing device configured for user interaction therewith. In various embodiments, a user computing entity 30 is coupled to, in communication with, and/or comprises an imaging apparatus 35. In various embodiments, the network 40 comprises one or more wired and/or wireless networks configured to enable electronic communication between a plurality of computing entities. Each of the components of the system (e.g., network computing entities 20 and/or user computing entities 30) may be in electronic communication with, for example, one another over the same or different wireless or wired networks 40 including, for example, a wired or wireless Personal Area Network (PAN), Local Area Network (LAN), Metropolitan Area Network (MAN), Wide Area Network (WAN), or the like. Additionally, while FIG. 1 illustrate certain system entities as separate, standalone entities, the various embodiments are not limited to this particular architecture.

Exemplary Network Computing Entity

FIG. 2 provides a schematic of a network computing entity 20 according to an example embodiment. In various embodiments, a network computing entity 20 trains a specimen analysis model using a machine learning technique. In various embodiments, a network computing entity 20 stores executable instructions for executing a machine learning-trained specimen analysis model. In various embodiments, a network computing entity 20 receives a specimen scoring request comprising specimen image data. In various embodiments, the network computing entity 20 executes the specimen analysis model to process the specimen image data and generate and/or determine respective specimen scores for each of one or more specimen for which the specimen image data comprises imaging data. In various embodiments, the network computing entity 20 is configured to generate and provide (e.g., transmit and/or cause display of) a specimen response including the respective specimen scores. In various embodiments, the network computing entity 20 is a server or Cloud-based computing resource. In an example embodiment, the specimen scoring request and/or specimen response is an application program interface (API) call and/or a call within a distributed application operating in part on the network computing entity 20 and in part on the user computing entity 30.

In general, the terms computing entity, entity, device, system, and/or similar words used herein interchangeably may refer to, for example, one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, scanners, televisions, dongles, cameras, wristbands, wearable items/devices, items/devices, vehicles, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the network computing entity 20 may also include one or more communications interfaces 220 for communicating with various computing entities, such as by communicating data, content, information, and/or similar terms used herein interchangeably that can be transmitted, received, operated on, processed, displayed, stored, and/or the like. For instance, the network computing entity 20 may communicate with other network computing entities 20, one or more user computing entities 30, and/or the like.

As shown in FIG. 2, in one embodiment, the network computing entity 20 may include or be in communication with one or more processing elements 205 (also referred to as processors, processing circuitry, and/or similar terms used herein interchangeably) that communicate with other elements within the network computing entity 20 via a bus, for example. As will be understood, the processing element 205 may be embodied in a number of different ways. For example, the processing element 205 may be embodied as one or more complex programmable logic devices (CPLDs), microprocessors, multi-core processors, coprocessing processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the network computing entity 20 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the network computing entity 20 may further include or be in communication with volatile media (also referred to as volatile storage, memory, memory storage, memory circuitry and/or similar terms used herein interchangeably). In one embodiment, the volatile storage or memory may also include one or more volatile storage or memory media 315 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, specimen analysis model program code, and/or the like may be used to control certain aspects of the operation of the network computing entity 20 with the assistance of the processing element 205 and operating system.

As indicated, in one embodiment, the network computing entity 20 may also include one or more communications interfaces 220 for communicating with various computing entities, such as by communicating data, content, information, and/or similar terms used herein interchangeably that can be transmitted, received, operated on, processed, displayed, stored, and/or the like. For instance, the network computing entity 20 may communicate with computing entities or communication interfaces of other network computing entities 20, and/or the like.

As indicated, in one embodiment, the network computing entity 20 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the network computing entity 20 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol. The network computing entity 20 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the network computing entity's 20 components may be located remotely from other network computing entity 20 components, such as in a distributed system. Furthermore, one or more of the components may be combined and additional components performing functions described herein may be included in the network computing entity 20. Thus, the network computing entity 20 can be adapted to accommodate a variety of needs and circumstances.

In example embodiments, the network computing entity 20 may be in communication with one or more other network computing entities 20 and/or one or more user computing entities 30. In example embodiments, the network computing entity 20 may be in communication with one or more other network computing entities 20 configured for executing, storing, managing, maintaining, and/or the like application program code corresponding to the transparent impact matrix platform, and/or the like.

b. Exemplary User Computing Entity

In an example embodiment, a user computing entity 30 may be a computing entity configured for user interaction (e.g., via a user interface thereof) for receiving, generating, and/or providing requests from a user to one or more network computing entities 20. In various embodiments, a user may be a person interacting with a user computing entity 30 (e.g., via the user interface thereof). For example, the user may be technician or medical service provider. In various embodiments, the user computing entity 30 is configured to obtain specimen image data (e.g., via or from one or more imaging apparatus 35), sample data (e.g., via a user input device), and/or the like; generate and provide a specimen scoring request; receive a specimen response comprising one or more specimen scores; and provide (e.g., via a user interface and/or display thereof) an IUI configured to provide one or more respective graphical representations of the one or more specimen scores.

FIG. 3 provides an illustrative schematic representative of a user computing entity 30 that can be used in conjunction with embodiments of the present invention. In various embodiments, a user computing entity 30 is configured to enable user interaction with the transparent matrix impact system and/or user experience (e.g., via an IUI) of one or more measures corresponding to one or more entities, locations, and/or processes of the transparent matrix impact system. As shown in FIG. 3, a user computing entity 30 can include an antenna 312, a transmitter 304 (e.g., radio), a receiver 306 (e.g., radio), and a processing device 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as another user computing entity 30, one or more network computing entities 20, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the user computing entity's 30 position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

As shown in FIG. 3, in one embodiment, the user computing entity 30 may include or be in communication with one or more processing devices 308 (also referred to as processing elements, processors, processing circuitry, and/or similar terms used herein interchangeably) that communicate with other elements within the user computing entity 30 via a bus, for example. As will be understood, the processing device 308 may be embodied in a number of different ways. For example, the processing device 308 may be embodied as one or more complex programmable logic devices (CPLDs), microprocessors, multi-core processors, coprocessing entities, application-specific instruction-set processors (ASIPs), and/or controllers. Further, the processing device 308 may be embodied as one or more other processing devices or circuitry. The term circuitry may refer to an entirely hardware embodiment or a combination of hardware and computer program products. Thus, the processing device 308 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing device 308 may be configured for a particular use or configured to execute instructions stored in volatile or non-volatile media or otherwise accessible to the processing device 308.

The user computing entity 30 may also comprise a user interface (that can include a display 316 coupled to a processing device 308) and/or a user input interface (coupled to a processing device 308). For example, the user interface may be an application, browser, user interface, dashboard, webpage, and/or similar words used herein interchangeably executing on and/or accessible via the user computing entity 30 to interact with and/or cause display of information. For example, the display 316 may be configured for providing (e.g., displaying) an IUI including one or more respective graphical elements indicating respective qualification criteria that were satisfied by item information corresponding to a particular item. The user input interface can comprise any of a number of devices allowing the user computing entity 30 to receive data and/or indications of user input, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect contextual information/data, telemetry, information/data, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

In example embodiments, the user computing entity 30 may be in communication with one or more network computing entities 20 and/or one or more other user computing entities 30. In example embodiments, the user computing entity 30 may be in communication with one or more network computing entities 20 configured for executing, storing, managing, maintaining, and/or the like application program code corresponding to the transparent impact matrix platform, and/or the like.

In various embodiments, a user computing entity 30 comprises, is coupled to, and/or is in communication with an imaging apparatus 35. In various embodiments, the imaging apparatus is configured to capture imaging data using vibrational microscopy and/or QPI imaging techniques. In various embodiments, the imaging apparatus 35 comprises a processing device 352. In various embodiments, the processing device 352 is configured to control operation of the imaging components 356 for capturing specimen imaging data and for causing communication of the specimen imaging data to the user computing entity 30. In various embodiments, the processing device 352 may be embodied as one or more complex programmable logic devices (CPLDs), microprocessors, multi-core processors, coprocessing processing device 352 may be embodied as one or more other processing devices or circuitry. The term circuitry may refer to an entirely hardware embodiment or a combination of hardware and computer program products. Thus, the processing device 352 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing device 352 may be configured for a particular use or configured to execute instructions stored in volatile or non-volatile media (e.g., memory 354) or otherwise accessible to the processing device 352.

The imaging apparatus can also include memory 354 such as volatile storage or memory and/or non-volatile storage or memory, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the image apparatus 35.

In various embodiments, the imaging apparatus 35 further comprises imaging components 356. The imaging components are operable (e.g., by the processing device 352) to cause the specimen image data to be captured. For example, the imaging components 356 comprise one or more light sources, one or more photodetectors (e.g., charge-coupled devices (CCDs), active pixel sensors (APSs) such as complementary metal-oxide-semiconductor (CMOS) sensors, and/or the like). For example, the imaging components 356 are configured to capture imaging data of one or more specimen via vibrational microscopy, QPI, bight field, and/or other imaging techniques. For example, as shown in FIG. 1, the imaging apparatus 35 comprises an opening, slot 36, and/or the like for receiving a slide 10 having specimen thereon. The imaging apparatus 35 then captures imaging data of the one or more specimen on the slide 10 using the imaging components 356 and provides the imaging data for receipt by the user computing entity 30.

c. Exemplary Networks

In one embodiment, any two or more of the illustrative components of the architecture of FIG. 1 may be configured to communicate with one another via respective communicative couplings to one or more networks 40. The networks 40 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 40 may have any suitable communication range associated therewith and may include, for example, global networks (e.g., the Internet), metropolitan area networks (MANs), wide area networks (WANs), local area networks (LANs), or personal area networks. In addition, the networks 40 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. Exemplary System Operation

Various embodiments provide methods, apparatuses, computer program products, systems, and/or the like that provide a specimen score for one or more specimen. For example, various embodiments provide a multi-modal machine learning system comprising a specimen analysis model and method for analyzing and aiding in the selection of high quality sperm for use in assisted reproduction technology (ART). The machine learning-trained specimen analysis model utilizes a plurality of sperm features derived from one or more imaging technologies such as vibrational spectroscopy and QPI to identify individual sperm with features associated with high rates of success in oocyte fertilization, embryo development, and live birth outcomes.

In various embodiments, the specimen analysis model is trained via a machine learning technique using features derived from training image data comprising vibration microspectroscopy and/or quantitative phase imaging (QPI) generated imaging data. Both methods are non-invasive, exhibit low photo-toxicity, and operate on label and/or dye-free specimens. These label and/or dye-free imaging methods avoid the use of macromolecular dyes or other contrast agents required by established fluorescence microscopy.

The vibrational microspectroscopy imaging technique generates spectral data of the target sperm indicating its molecular composition at various sample points. The QPI imaging method generates a quantitative map of local phase shifts in the sample. The phase map can be interpreted and constructed either as 2D or 3D feature input to the specimen analysis model characterizing various features of the respective specimen, including the morphology and related physical properties such as biomass.

In various embodiments, the specimen analysis model is a multi-modal machine learning-trained model as it incorporates multiple imaging modalities as input features of specimens during training and inference. These modalities can be extended to include input features from bright field images or videos (e.g., time ordered sequences of imaging data) derived from an ordinary light microscopy and non-imaging sample data both from the sperm donor or if known the intend egg donor. For example, the sample data provides source information (e.g., medical and/or family history, demographics, and/or the like) corresponding to the source or donor of the sperm, egg, and/or the like for use in the fertilization event.

Imaging methods can be extended to capture imaging data through time, in various embodiments. Tracking sperm movement, morphological rigidity, and/or other traits that are observable over time (e.g., on a time scale of a few seconds to a few minutes) provide greater predictive power on molecular composition. Each modality provides additional context on the sperm sample that in concert enables the specimen analysis model to learn the combination of features associated with successful fertilization, embryo development, and live birth outcomes.

In various embodiments, the specimen analysis model is a deep learning neural network. In general deep learning neural networks are a subset of machine learning models that are structured in multiple layers with potentially many parameters to optimize (e.g., through a machine learning training process). In various embodiments, the specimen analysis model comprises an input layer configured to receive specimen imaging data or one or more imaging types (e.g., vibrational microspectroscopy, QPI, and/or other non-invasive imaging techniques), sample data, and/or other input. The specimen analysis model further comprises a representation layer. For example, based on various parameters and/or weights of the specimen analysis model, the specimen analysis model is configured to transform the input received via the input layer into a feature representation of the respective specimen at the representation layer. The specimen analysis model further comprises a prediction layer. For example, based on various parameters and/or weights of the specimen analysis model, the specimen analysis model is configured to transform the feature representation of the respective specimen at the representation layer to a prediction at the prediction layer. The specimen analysis model further comprises an output layer configured to provide the specimen score determined based on the imaging data, sample data, and/or the like. For example, based on various parameters and/or weights of the specimen analysis model, the prediction at the prediction layer of the specimen analysis model is transformed into an specimen score that is provided as an output of the specimen analysis model at the output layer.

A technical challenge in the specimen analysis model training is limited access to positive target labels from successful in vitro fertilization (IVF) outcomes associated with the specific sperm used in fertilization. This is particularly a problem in the deep learning neural networks. In various embodiments, a technical solution to this technical challenge is provided through the use of a semi-supervised training technique to train the specimen analysis model. In various embodiments, self-supervision is incorporated into the loss function for pre-training the specimen analysis model. This includes a contrastive or metric learning strategy where the specimen analysis model's parameters are trained to distinguish between input features gathered from the same sperm as a positive target and those from different sperm as a negative target. The sperm features are collected repeatedly at different time points from the same sample to expand the dataset allowing for multiple combinations of positive-positive pairings. Negative examples maybe selected randomly amongst a negative candidate set of sperm. The negative set can be updated and weighted to select for negative target examples that has caused confusion throughout training, that is, we can actively select for negative samples that our model is most likely to incorrectly classify as a positive sample.

The self-supervised pre-training step encourages model parameterization that selects for features elements that are best able to distinguish between sperm samples. In various embodiments, the representation layer captures an efficient representation of the specimen (e.g., an individual sperm) as an array of numeric values equal to the size (e.g., number of nodes) in the representation layer. In various embodiments, the representation layer is a fully connected layer of the specimen analysis model that is located between the input layer and the prediction layer. The representation of the specimen at the representation layer is a learned feature embedding of the specimen (e.g., the individual sperm). This feature embedding can be used as the basis for organizing and identifying specimen with similar attributes which can be predictive of success in fertilization of eggs, embryo development, and live birth.

In various embodiments, the training process for the specimen analysis model includes multi-variable clustering on the learned feature embeddings to generate groupings or clusters of sperm that are generalizable across sperm donors. When new specimen imaging data is provided as input to the specimen analysis model, the specimen analysis model determines the sperm feature embedding based on the learned parameters and/or weights of the specimen analysis model. This feature embedding is then assigned to a learned cluster based on an embedding distance from cluster centers or other similarity metrics to determine a prediction for the specimen. In various embodiments, each cluster is assigned a respective specimen score based on the member sperms known success rates in IVF or other factors associated with successful fertilization, embryo development, and live birth outcomes. Thus, the specimen score for a respective specimen is determined based on the cluster to which the feature embedding was assigned, in an example embodiment.

In various embodiments, the sperm feature embedding can utilize feature reduction techniques as a post-processing step to reduce the size of the representation and increase the speed of embedding comparisons including quantization methods and principal component analysis (PCA).

In various embodiments, an alternative self-supervised sperm feature embedding method utilized either as a substitute for or in conjunction with the contrastive and similar metric loss methods described above, is an autoencoding strategy. In this encoder-decoder architecture, feature inputs are compressed into a smaller central layer of a deep learning specimen analysis model in the encoding stage and expanded out to the original feature input dimensions in the decoding stage. The specimen analysis model is optimized to reduce the reconstruction loss of the original input features. In the case of image maps or time series content, the reconstruction error can be calculated for either the full input data or masked patches. The central layer is a representative embedding of the sperm input features that minimize reconstruction loss. This representation is generated from the encoder stage of the specimen analysis model. The learned weights and/or parameters of the specimen analysis model trained for generating the sperm feature embedding from the received input can be used to characterize the most relevant features of an individual sperm.

In various embodiments, sperm feature embeddings can be used as the basis to determine similarity between individual sperm which can be used to find similar sperm in a dataset with known fertility outcomes or attributes. An individual sperm from a patient sample can be selected for use in a fertilization event based on how similar it is to sperm in the known dataset that are correlated to success in IVF and related ART technologies.

In various embodiments, machine learning models generating sperm feature embeddings are used as the basis for further supervised training of the specimen analysis model. Supervised training can either be used to improve the sperm feature embeddings or to predict for specific attributes or outcomes of a fertilization event. Machine learning optimization targets relevant to quality sperm selection and available to utilize in model training include DNA fragmentation level; sperm karyotype; presence of karyotype abnormalities; chromosomal gender; known disease or fertility of donor; presence or absence of specific genes or epigenetic mechanisms associated with poor fertilization, miscarriage, or disease; morphological abnormalities of the sperm; sperm motility measures; and/or the like. These optimization targets can be used as part of a single loss function where the specimen analysis model aims to predict accurately across one or more of the targets and use the combined loss to update the model parameters and/or weights during training iterations. The targets can also be used to train independent models that can be used to predict target sperm attributes independently, as well as an over-all quality score with a weighted ensemble of the independent sub-models as inputs. For example, the specimen analysis model comprises a plurality of independent target sperm attribute models that each generate respective target scores, in an example embodiment. These target scores are then combined, aggregated, and/or the like to generate the specimen score corresponding to the individual sperm. These supervised training methods can be employed with or without the pre-training phase.

In various embodiments, the specimen analysis model is fine-tuned based on a global optimization target of successful IVF outcomes measurable by a variety of methods including successful fertilization, embryo development, blastocyst formation, genetic testing of the embryo, and live birth outcomes. This can apply to a single overarching model or an ensemble of independent target sperm attribute models.

In various embodiments, the specimen analysis model uses a deep learning neural network as model architecture. In an example embodiment, the specimen analysis model comprises a convolutional neural network (CNN) used to input specimen imaging data adjusted to support the feature dimensions of the input source. In an example embodiment, one or more vision transformers are used as an alternative image based deep learning architecture that is utilized either as a replacement or in conjunction with CNNs to adjust the specimen imaging data for processing by the specimen analysis model. In various embodiments, a fully connected input layer is used to ingest input data such as sample data and/or other non-image data (e.g., medical and/or family history, demographics, and/or the like). In various embodiments, the sample data includes categorical, ordinal, or interval data. In various embodiments, a recurrent neural network (RNN) architecture is utilized prepare and/or ingest timeseries input data, such as video or our other specimen imaging data captured through time.

In various embodiments, variations of specimen analysis model architecture support training and predicting sperm quality or associated sperm attributes with any combination of imaging features and patient data, including selecting a single imaging feature as a standalone input to the specimen analysis model.

In various embodiments, the network computing entity 20 performs the machine learning process to train the specimen analysis model. In various embodiments, the machine learning-trained specimen analysis model is stored by a cloud-based server (which may be a network computing entity 20).

The network computing entity 20 receives specimen scoring requests generated and/or provided by a user computing entity 30 that is disposed at the clinical site where the specimen is located and imaged, in various embodiments. In various embodiments, the specimen scoring requests include input features (e.g., specimen imaging data, sample data, and/or the like), a device identifier configured to identify the user computing entity 30 and/or imaging apparatus 35 used to generate the specimen imaging data, and a generated request id configured to identify the particular specimen scoring request. In various embodiments, the input features include specimen imaging data (e.g., imaging input features) and, in some embodiments, additional technician supplied input features such as sample information such as source information (e.g., medical and/or family history, demographics, and/or the like corresponding to the donor) corresponding to the source or donor of the sperm. In an example embodiment, the specimen scoring request further includes a unique patient identifier configured to identify the patient (e.g., sperm donor, IVF recipient, and/or the like) and/or an authorization token for secure communication. Security protocol will be consistent with medical best practices for data management and communication. For example, the network computing entity 20 is configured to verify the request authorization token, in an example embodiment, prior to generating a specimen score by processing the input features using the specimen analysis model.

In various embodiments, each specimen score is be recorded and associated with the request id, and optionally a network computing entity 20 generated unique identifier, and timestamp of the specimen scoring request. For example, the network computing entity 20 may store a database of generated specimen scores that comprises records that include a respective specimen score, request id, network computing entity 20 generated unique identifier, timestamp of the specimen scoring request, and/or the like. Additional information provided by the specimen scoring request (e.g., the patient identifier, device identifier, and/or the like) is also stored in association with the generated specimen score when available. In various embodiments, the input features provided by the specimen scoring request are stored to an appropriate database and/or datastore (e.g., stored in memory 210, 215) based on input type and referenceable to the request and model prediction through associated identifiers in the database (e.g., request identifier, network computing entity generated unique identifier, and/or the like).

In various embodiments, embryology lab personnel and/or medical service providers are able to access the specimen scores via an on-device user-interface (UI) or web portal of the user computing entity 30, for example. In various embodiments, embryology lab personnel and/or medical service providers may associate additional sample data such as patient data (e.g., donor age, fertility history, smoking status, and/or the like) before model inference to use as additional input features or after inference to modify the specimen score and positive outcome probability assessment.

In various embodiments, authorized users can create a placeholder request in the web portal or on-device UI which will generate a unique ID. If created in the web portal page this id can be associated with a specimen scoring request via the user computing entity 30 UI. In various embodiments, a user is required to login and perform an authentication associated with the user and facility to access the web portal and/or UI. The web portal and/or UI can also be used to review past specimen scores, specimen imaging data, and associated sample information. Specimen scores for individual sperm for a single sperm donor can be aggregated to compute the overall quality of the donor's sperm. Future ART success metrics can be added to the portal and associated with a selected sperm used in fertilization, such that the system is enabled to collect on-going clinical data from a plurality of lab facilities. This on-going collection of clinical data enables future specimen analysis model retraining and/or refinement.

In various embodiments in which the specimen analysis model is stored and executed by the network computing entity 20 (e.g., possibly a Cloud-based computing resource or server), the specimen analysis model may be updated dynamically without requiring replacement or updating the user computing entity 30. In an example embodiment, the specimen analysis model is stored in part or in full by the user computing entity 30 and executed thereby. A specimen analysis model, partial model or pre-processing portion of the specimen analysis model can be updated with a new model or computational algorithm from the network computing entity 20 as appropriate. For example, the user computing entity 30 may regularly or periodically check to see whether updates are available, check for updates in response to receiving and/or generating a specimen scoring request. In an example embodiment, the network computing entity 20 may push updates to the user computing entity 30. Specimen analysis model version identifiers may be stored in the database in association with their respective predictions.

In various embodiments, the user computing entity 30 comprises, is in communication with, and/or is coupled to the imaging apparatus 35. In various embodiments, the imaging apparatus 35 comprises imaging components 356 such as the imaging optical and spectrographic components as well as the capture sensors and excitation source or sources. In various embodiments, the imaging apparatus 35 includes a dedicated slot 36 configured to receive therein a microfluidic chip or specimen slide 10. The imaging apparatus 35 optionally has environmental controls allowing simulation of the in-utero environmental temperatures (e.g., within the slot 36 of the imaging apparatus 35 and/or within the room in which the user computing entity 30 is disposed). The specimen slot 36 can be enclosed to isolate it from the outside environment providing a consistent setting for imaging minimizing environmental light interference. The temperature controls also ensure consistency in sperm behavior as temperature variance can alter the sperms' swimming behavior, imaging, and spectral readings. This consistency is essential in ensuring accurate specimen scores that are consistent across lab facilities.

A display 316 of the user computing entity 30 can be caused to display sperm sample information, including patient and sample identifiers. It can also display specimen score results which are associated with individual sperm positions in the microfluidic chip or sample slide 10. In an example embodiment, the display 316 is a touch screen enabling technician input on the display or a separate alphanumeric keypad 318 can be utilized. In various embodiments, communication between the user computing entity 30 and the imaging apparatus 35 and/or between the user computing entity 30 and other computing entities is authenticated using security practices configured to provide patient data security. In various embodiments, the user computing entity 30 and the imaging apparatus 35 communicate with one another directly through a wired protocol or wireless protocol or mediated through a cloud-based server which will serve data and manage user input through a secure web portal or mobile application.

In various embodiments, the imaging apparatus 35 is configured to perform various types of imaging. In an example embodiment, the imaging apparatus 35 is configured to perform at least one of vibrational spectroscopy or quantitative phase imaging. In various embodiments, the vibrational spectroscopy includes at least one of Raman microspectroscopy or IR microspectroscopy. These vibrational microspectroscopy and quantitative phase imaging are non-destructive and label-free imaging techniques.

Raman microspectroscopy combines an optical microscope with an excitation source, such as a laser, and a Raman spectrometer. When the imaging apparatus 35 is configured to perform Raman microspectroscopy, the imaging components 356 comprise a Raman spectrometer that captures Raman scattering where light from the excitation source is projected onto the sperm sample and a small percentage of the light is scattered inelastically emitting at frequencies different from the incident light. The Raman spectrometer measures this Raman shift from the wavelength of the excitation source. It separates the scattered light emitted from the sperm sample into component wavelengths which is then focused on to a sensor, such as a charge-coupled device (CCD) complementary metal-oxide-semiconductor sensor (CMOS), and/or the like. The sensor is read by processing device 352 or processing device 308. These values capture the intensity of the scattered light at various frequencies and are typically expressed in wavenumbers, which is the light frequency as a function of the excitation source frequency. The resulting spectra is a fingerprint of the molecular composition of the sperm sample at the point of sampling. Multipoint sampling is used to capture molecular composition features along different areas of the sperm. A systematic sampling along a 2D grid to generate a rasterized multidimensional image with spectral fingerprint at each point is used, in various embodiments. Fixed positions of isolated sperm on a slide with input wells or micro-fluidic channels allow for selective grid sampling around regions likely to hold isolated sperm. In another example embodiment, the sampling either randomly or selectively captures points at different regions of a sperm. Alternatively, a global grid of sample points containing many sperm samples disposed on the same slide 10 can be collected. These can be split into image segments of individual sperm in image post processing by the user computing entity 30 or the network computing entity 20 prior to processing of the specimen imaging data by the specimen analysis model. The following extensions of Raman microspectrometer can be applied independently or in tandem.

Shifted-excitation Raman difference spectroscopy (SERDS) is a form of Raman spectroscopy that addresses excitation induced background fluorescence, which is a source of interference on the baseline molecular signals. In SERDS, Raman imagining is repeated over the same points with a small shift in excitation frequency. The Raman peaks shift with the changing excitation frequency whereas the broad fluorescence background does not change. Post-processing to eliminate the fluorescence signal in the Raman spectra can be done explicitly by the user computing entity 30 or the network computing entity 20. In an example embodiment, fluorescence removal can be implicitly learned by the specimen analysis model through the machine learning process, where raw Raman spectra signals from the shifted frequency excitation are sent and used as separate features or channels in the machine learning model input during training. Excitation at multiple different frequencies of a sample point is a possible extension of the Raman imaging technique.

In an example embodiment, to further improve microspectroscopy imaging time, the grid sampling region around a sperm can be reduced through use of sperm object detection. A machine learning model such as a convolutional neural network (CNN) is trained to identify the bounding box of a sperm or identify pixels likely to contain sperm on brightfield photographic images or videos of the sampling area. Sperm object detection of the images can be done through the imaging apparatus 35, user computing entity 30, or network computing entity 20, in various embodiments. For example, the imaging components 356 may include an on-device camera for use with standard light microscopy for image capture. The determined and/or generated bounding boxes of pixels is used to reduce the area needed for more the time consuming vibrational microspectroscopy or quantitative phase imaging. For example, the specimen imaging data may be captured within the bounding box(es) and not outside thereof.

Human controlled targeting to define the Raman sampling region around select sperm is applied, in an example embodiment. In this case, bright field images or videos derived from an ordinary light microscopy (e.g., of the imaging components 356) can be utilized by the technician to manually identify the region of interest (e.g., via a display 316, user input device, and/or the like). The sample slide 10 or micro-fluidic device can be manually shifted into to a target zone. Alternately the technician can input the region of interest via the display 316, user input device of the user computing entity 30 and/or imaging apparatus 35, and/or the like. The target area information will be transmitted to the on-board imaging control system executed by the processing device 352 to define the Raman sampling.

Other Raman techniques used in various embodiments include Coherent Anti-stokes Raman scattering (CARS) and Surface enhanced Scattering (SERS). CARS utilizes three excitation beams, a pump beam, a Stokes beam, and a probe beam at different frequencies. These beams interact with the sample generating an enhanced anti-Stokes Raman signal that is the bases for increased vibrational contrast. SERS amplifies Raman signals from molecules by several orders of magnitude. It relies on the presence of rough metal surfaces or by metal colloidal nanoparticles that induce much higher scattering efficiencies in molecules.

Alternative excitation sources (e.g., for us in various Raman techniques and/or other imaging techniques) to lasers such as LEDs are used in various embodiments. While LED excitation is generally considered to produce less precise signals, their use as a replacement may further decrease any effects on living gametes.

The Raman microspectropic fingerprint can be associated with sperm karyotype abnormalities, issues with protein folding around DNA, structural problems in the autosomal region, the mitochondrial tail, or elsewhere in the sperm, and other features that can be linked with performance in fertilization, embryo development, and live birth outcomes through learned parameters and/or weights of the specimen analysis model.

Quantitative phase imaging (QPI) or quantitative phase contrast microscopy is a group of imaging techniques that quantify the phase shift that occurs when light waves pass through a specimen. QPI operate on unlabeled specimens, exhibit low phototoxicity, and no photobleaching. QPI relies on two beams of light: a sample beam which passes through the specimen and a reference beam which does not. Contrast is generated from optical pathway lengths changes (phase shifts) between the beams caused by changes in thickness and refractive index in the sample. The images produced represent quantitative maps of the local phase shifts in the sample sperm. The quantitative map of sperm specimen can be converted to local thickness, refraction index, and dry mass maps of the sperm. The quantitative map can capture a single 2D plane of the sperm, 3D volumetric information, or add an additional dimension of observational data through time. This data is used as input for training and inferences in the specimen analysis model either stand alone or coupled with feature data from other imaging sources and source information. Various embodiments may use various implementations of QPI including spatial light interference microscopy (SLIM), gradient light interference microscopy (GLIM), white light diffraction phase microscopy (wDPM), and/or Digital holographic microscopy (DHM).

In an example embodiment, the imaging apparatus 35 is configured to perform fluorescence lifetime imaging (FLIM). In general, FLIM measures the time a fluorophore remains in an excited state before emitting a photon. Sperm are rich in endogenous fluorophores that can be used for label-free autofluorescence molecular imaging via FLIM. Endogenous fluorophores are biomarkers whose emission properties are impacted by their microenvironment, morphology, metabolic state, and pathological conditions of a sample. The most common implementation of FLIM is Time-Correlated Single-Photon Counting (TCSPC). TCSPC measures the time between a sample excitation by a pulsed laser and the arrival of the emitted photon at the detector. This time delay is measured repeatedly to account for statistical variation in fluorophores emission. These repeated time measures can be recorded in a histogram. In scanning a sperm sample an image can be constructed such that each pixel is a unique histogram corresponding to a point on the sample. In various embodiments, the specimen analysis model is trained to receive FLIM imaging data as input. For example in various embodiments, the specimen imaging data comprises FLIM imaging data that is provided to the specimen analysis model as input for use in determining the respective specimen score.

In various embodiments, the imaging apparatus 35 is configured to perform bright-field (BF) microscopy. In BF microscopy, illumination light is transmitted through the specimen and the contrast is generated by the absorption of light in dense areas of the specimen. Standard BF images or videos are captured as an additional feature input to the machine learning model which can provide additional context for training of the specimen analysis model and/or as part of the specimen imaging data provided as input to the specimen analysis model. This imaging or video can also be utilized by embryologist, technicians, or medical service providers as a visual supplement to communicate selection or rejection outcomes associated with a particular sperm sample.

In various embodiments, the sperm sample is separated into individual sperm for evaluation (e.g., imaging) and selection.

While imaging can be done for each sperm individually or in a cohort of sperm at once, the physical separation of sperm allows for easy association of prediction results and retrieval of a selected sperm by embryologist or lab technicians. It also prevents spatial overlapping of the sperm during imaging, which limits confusion in imaging signals including vibrational spectral and phase signals.

In the simplest form this separation can be done by the embryologist or lab technician. The lab technician reviews a sperm sample under a microscope and individually selects candidate sperm, which they isolate and add to the slide 10 for imaging by the imaging apparatus 35 and analysis by the specimen analysis system. For example, the slide 10 may be similar to that illustrated in FIG. 4A. For example, the illustrated slide 400 or plate contains separate wells 405 (e.g., 405A, 405B, 405C, 405D) to hold each selected sperm in isolation. The fixed well position ensures the resulting specimen scores are associated with a specific well and sperm. It also enables consistent positioning of sperm for imaging and limits mixing of signals between sperm samples. In an example embodiment, the slide 400 further includes human-readable well identifiers 408 to further simplify identification of which sperm on the slide 400 corresponds to which returned specimen score.

A variant for sperm isolation utilizes a microfluidic chip 410, an example of which is illustrated by FIG. 4B. The microfluidic chip 410 allows the system to separate the individual sperm from a sperm sample. An embryologist or lab technician places an aliquot of sperm in an input well 412. Channels 414 running from the well 412 have openings that allow the sperm to freely swim down the channels 414. Channels 414 can be sized to allow only one sperm at a time to swim down. Once in a single sperm channel 414, the sizing will make it difficult for the sperm to turn around and swim in the reverse direction. The opening of the channels 414 can optionally be wider to encourage the entrance of motile sperm. The end of the channels optionally contains a small well 415 (e.g., 415A, 415B) sized to fit only one sperm. The channels can also simply end or reduce in diameter until the sperm is no longer able to make forward progress and is stuck in place. The channels 414 are in a branching pattern, in the illustrated embodiment, with larger channels allowing many sperm at once to flow splitting to increasingly smaller channels until a channel can only fit one sperm at time. The branching pattern randomly divides the sperm down the different splits. It ends in leaf wells that fit single sperm or channel branches too small for the sperm to make forward progress. The microfluidic mechanism can be passively driven through the sperms own swimming. It alternatively can be actively driven through flow driven microfluidics. In the flow driven embodiment, mechanic sperm are pushed along the channel paths through the flow of the liquid medium in which the sperm swim. This encourages sperm to move toward the end of the channels or branches. It also can hold the sperm in place at channel and branch ends. The flow stream can be driven by hydraulic pressure initiated by capillary forces and gravity, eliminating the need for an external power source or controlled by mechanical pumping or suction. For example, the branches 414 may extend down into the medium of the microfluidic chip 410 such that gravity can drive the microfluidic mechanism. Sperm swimming can optionally be held in place by microfluidic gates. Selective drainage of the liquid medium can also be used to isolate and fixed sperm in a given position. Activation of drainage or medium flow can be controlled by a timer, visual assessment of the embryologist or lab technician, or control by the device using sensors or image analysis to detect sperm position. For example, imaging data captured by the imaging apparatus 35 may be used to track a sperm's movement along the microfluidic chip's channels 414 and sent as feature input as part of the specimen imaging data provided as input to the specimen analysis model.

Example Operation of Network Computing Entity

FIG. 5 provides a flowchart illustrating various processes, procedures, operations, and/or the like performed by a network computing entity 20, for example, to train and use a specimen analysis model to provide specimen scores (e.g., in response to receiving and/or processing specimen scoring requests). Starting at step/operation 502, initial training data is collected and/or generated. For example, the network computing entity 20 may access one or more databases or other datastores storing specimen imaging data for a plurality of specimen, possibly in association with respective sample data providing source information (e.g., medical and/or family history, demographics, and/or the like corresponding to the donor) for the corresponding specimen, and respective outcome indications that indicate an outcome of a respective fertilization event (e.g., was the fertilization successful or unsuccessful in terms of oocyte fertilization, embryo development, and/or live birth outcome) in which the respective specimen was used. In various embodiments, the specimen imaging data corresponds to at least one type of imaging, with the at least one type of imaging comprising vibrational microspectroscopy and/or QPI. In an example embodiment, the initial training data may include multiple instances of specimen image data that comprise imaging data of a same sperm captured at different points in time. In various embodiments, the initial training data is collected and/or generated based on user input received via a user input device of the network computing entity 20 and/or user computing entity 30.

At step/operation 504, the network computing entity 20 pre-train the specimen analysis model. For example, the architecture of the specimen analysis model is defined and the parameters and/or weights of the specimen analysis model or initialized to random values (possibly within a set range). The parameters and/or weights of the specimen analysis model are then determined through a training process in which the specimen analysis model is used to process instances of the initial training data, determine a specimen score based thereon, and then determine a loss function value. The parameters and/or weights of the specimen analysis model are modified, adjusted, and/or updated based on the loss function value so as to minimize the loss function value through the iterative machine learning process, as described above.

Once the pre-trained specimen analysis model satisfies a convergence criterion (e.g., the loss function value of an iteration and the subsequent iteration is within a threshold difference for a threshold number of iterations), it is determined that the pre-trained specimen analysis model is successfully pre-trained.

At step/operation 506, the network computing entity 20 collects and/or identifies additional training data. In various embodiments, at least a portion of the additional training data is collected as a result of a notification of being provided to a user (e.g., via a user interface of the network computing entity 20 and/or via display 316 of a user computing entity 30) indicating that additional training data is needed and possibly indicating morphological features of specimen for which additional training data should be captured and provided. One or more user computing entities 30 may then be operated (e.g., by respective technicians and/or medical service providers) to capture the additional training data. In various embodiments, the additional training data is identified from one or more datastores using the self-supervised mechanism disclosed above. For example, negative examples maybe selected randomly amongst a negative candidate set of sperm. The negative set can be updated and weighted to select for negative target examples that has caused confusion throughout training, that is, the network computing entity 20 can actively select for negative samples that the specimen analysis model is most likely to incorrectly classify as a positive sample.

For example, the network computing entity 20 may access one or more databases or other datastores storing specimen imaging data for a plurality of specimen, possibly in association with respective sample data providing source information (e.g., medical and/or family history, demographics, and/or the like corresponding to the donor) for the corresponding specimen, and respective outcome indications that indicate an outcome of a respective fertilization event (e.g., was the fertilization successful or unsuccessful in terms of oocyte fertilization, embryo development, and/or live birth outcome) in which the respective specimen was used to collect and/or identify additional training data. In various embodiments, the specimen imaging data corresponds to at least one type of imaging, with the at least one type of imaging comprising vibrational microspectroscopy and/or QPI. In an example embodiment, the additional training data may include multiple instances of specimen image data that comprise imaging data of a same sperm captured at different points in time. In various embodiments, the additional training data is collected and/or identified based on user input received via a user input device of the network computing entity 20 and/or user computing entity 30.

At step/operation 508, the specimen analysis model may be trained and/or fine-tuned. For example, a machine learning process may be initiated by initializing the weights and/or parameters of the specimen analysis model based on the weights and/or parameters of the pre-trained specimen analysis model. The machine learning process may then proceed by using the additional training data to train the specimen analysis model (e.g., to optimize the weights and/or parameters thereof so as to minimize a loss function). Once the machine learning-trained specimen analysis model satisfies a convergence criterion (e.g., the loss function value of an iteration and the subsequent iteration is within a threshold difference for a threshold number of iterations), it is determined that the machine learning-trained specimen analysis model is trained.

In various embodiments, the specimen analysis model is trained such that input corresponding to a particular specimen and received via the input layer thereof (e.g., comprising specimen imaging data or one or more imaging types, sample data, and/or other input) is transformed into a feature representation of the respective specimen at the representation layer. The specimen analysis model is further trained to generate clusters of feature representations based on the feature representations and such that each cluster corresponds to similar outcomes (e.g., a range of probably of positive successful fertilization, embryo development, or live birth outcomes). For example, the specimen analysis model is trained to determine a cluster to which a particular specimen corresponding to a respective input corresponds at the prediction layer. The specimen analysis model is further trained to, based on the cluster to which the particular specimen was assigned, determine a specimen score for the particular specimen and provide the specimen score via the output layer. The weights and/or parameters of the machine learning-trained specimen analysis model are then stored by the network computing entity 20, provided for storage and use to the user computing entity 30, and/or the like.

At some point in time after the training of the specimen analysis model, the network computing entity 20 receives a specimen scoring request. For example, at step/operation 512, the network computing entity 20 receives a specimen scoring request. For example, a user computing entity 30 generates and provides a specimen scoring request, such that the network computing entity 20 receives the specimen scoring request (e.g., via a communications interface 220 thereof). In an example embodiment, the specimen scoring request is received via an API call, via a distributed application operating in part on a user computing entity 30 and in part on a network computing entity 20, and/or the like.

In various embodiments, the specimen scoring request includes input features corresponding to one or more specimen (e.g., specimen imaging data, sample data, and/or the like), a device identifier configured to identify the user computing entity 30 and/or imaging apparatus 35 used to generate the specimen imaging data, and a generated request id configured to identify the particular specimen scoring request. In various embodiments, the input features include specimen imaging data (e.g., imaging input features) for one or more specimen and, in some embodiments, additional technician supplied input features such as sample data for the one or more specimen such as source information (e.g., medical and/or family history, demographics, and/or the like) corresponding to the source or donor of the one or more specimen. In an example embodiment, the specimen scoring request further includes a unique patient identifier configured to identify the patient (e.g., sperm donor, egg donor, IVF recipient, and/or the like) and/or an authorization token for secure communication. For example, the network computing entity 20 is configured to verify the request authorization token, in an example embodiment, prior to generating a specimen score by processing the input features using the specimen analysis model.

In various embodiments, each specimen score is be recorded and associated with the request id, and optionally a network computing entity 20 generated unique identifier, and timestamp of the specimen scoring request. For example, the network computing entity 20 may store a database of generated specimen scores that comprises records that include a respective specimen score, request id, network computing entity 20 generated unique identifier, timestamp of the specimen scoring request, and/or the like. Additional information provided by the specimen scoring request (e.g., the patient identifier, device identifier, and/or the like) is also stored in association with the generated specimen score when available. In various embodiments, the input features provided by the specimen scoring request are stored to an appropriate database and/or datastore (e.g., stored in memory 210, 215) based on input type and referenceable to the request and model prediction through associated identifiers in the database (e.g., request identifier, network computing entity generated unique identifier, and/or the like).

At step/operation 514, the network computing entity 20 extracts the input features (e.g., specimen image data, sample data, and/or the like) from the specimen scoring request for a particular and/or individual specimen of the one or more specimen and provides the input features to the input layer of the specimen analysis model. The specimen analysis model then processes the input features by transforming the input features received via the input layer thereof, to a trained feature embedding at the representation layer, to a prediction (e.g., cluster assignment) at the prediction layer, to a specimen score a the output layer by applying the weights and/or parameters of the specimen analysis network learned via the machine learning training process. Thus, the network computing entity 20 executes the specimen analysis model to process the input features corresponding to an individual specimen of the one or more specimen to determine a respective specimen score. If the specimen scoring request comprises specimen imaging data for a plurality of specimen (e.g., two or more) the specimen scores of individual specimen of the plurality of specimen may be determined in parallel (e.g., by different instances of the specimen analysis model), in series, or a combination thereof.

At step/operation 516, the network computing entity 20 generates and provides a specimen response comprising a specimen score for at least one and/or each of the one or more specimen for which input features were provided by the specimen scoring request. For example, a network computing entity 20 generates and provides a specimen response (e.g., via communications interface 220), such that the user computing entity 30 receives the specimen response (e.g., via a network interface 320 and/or receiver 306 thereof). In an example embodiment, the specimen response is received via an API call, API response via a distributed application operating in part on a user computing entity 30 and in part on a network computing entity 20, and/or the like.

In various embodiments, the specimen response comprises a specimen score for at least one of the one or more specimen, the request identifier that was included in the corresponding specimen scoring request, a patient identifier, an indication of which specimen (e.g., the inhabitant of which well of the slide 10) that each of the specimen scores corresponds, and/or the like. In various embodiments, the specimen response is provided by the network computing entity 20 in real time or near real time with respect to the receipt of the corresponding specimen scoring request.

In an example embodiment, the specimen response is access "on-demand" via a web portal or user interface (e.g., of the distributed application) operating on the suer computing entity 30. For example, in various embodiments, the network computing entity 20 stores the specimen score to a database in association with a specimen identifier, request identifier, patient identifier, the input features, and/or the like as described above. An authorized user (e.g., operating a user computing entity 30) may then access the specimen score via a web portal or user interface (e.g., provided by a portion of the distributed application operating on the user computing entity 30) to access the specimen score.

Example Operation of User Computing Entity

FIG. 6 provides a flowchart of various processes, procedures, operations, and/or the like performed by a user computing entity 30 to provide respective specimen scores for one or more specimen. Starting at step/operation 602, the user computing entity 30 obtains sample data. In various embodiments, the sample data provides source information (e.g., medical and/or family history, demographics, and/or the like corresponding to the donor) for one or more specimen. For example, a technician or medical service provider operating the user computing entity 30 may provide and/or enter at least a portion of the sample data via a user input device of the user computing entity 30. In another example, a technician or medical service provider operating the user computing entity 30 may provide and/or enter a patient identifier (e.g., identifying the donor) to cause the sample data providing source information for the one or more specimen to be accessed from a donor database, for example.

At step/operation 604, the user computing entity 30 obtains specimen imaging data for one or more specimen. For example, the user computing entity 30 receives the specimen imaging data from the imaging apparatus 35. In various embodiments, the user computing entity 30 controls operation of the imaging apparatus 35 so as to cause the imaging apparatus 35 to capture and provide the specimen imaging data.

In various embodiments, the specimen imaging data comprises imaging data for one or more specimen of at least one imaging type. The at least one imaging type is vibrational microspectroscopy or QPI. In various embodiments, additional types of imaging data corresponding to the one or more specimen may also be obtained (e.g., FLIM imaging data, BF microscopy imaging data, and/or the like).

In various embodiments, the user computing entity 30 performs or controls operation of the imaging apparatus 35 to cause the imaging apparatus 35 to perform pre-processing of the specimen image data. For example, the pre-processing of the image data may include background fluorescence removal, partitioning of imaging data captured of a slide 10 including multiple specimen into individual specimen imaging data, and/or the like.

In various embodiments, step/operation 602 and 604 may be performed simultaneously or in the opposite order illustrated in FIG. 6.

At step/operation 606, the user computing entity 30 aggregates the specimen image data and any corresponding sample data to generate a specimen scoring request. In various embodiments, the specimen scoring request includes input features corresponding to one or more specimen (e.g., specimen imaging data, sample data, and/or the like), a device identifier configured to identify the user computing entity 30 and/or imaging apparatus 35 used to generate the specimen imaging data, and a generated request id configured to identify the particular specimen scoring request. In various embodiments, the input features include specimen imaging data (e.g., imaging input features) for one or more specimen and, in some embodiments, additional technician supplied input features such as sample data for the one or more specimen such as source information (e.g., medical and/or family history, demographics, and/or the like) corresponding to the source or donor of the one or more specimen. In an example embodiment, the specimen scoring request further includes a unique patient identifier configured to identify the patient (e.g., sperm donor, egg donor, IVF recipient, and/or the like) and/or an authorization token for secure communication.

The user computing entity 30 provides (e.g., transmits) the specimen scoring request (e.g., via network interface 320 or transmitter 304) for receipt by the network computing entity 20. The network computing entity 20 receives the specimen scoring request and processes the input features corresponding to the one or more specimen and included in the specimen scoring request using the specimen analysis model to generate respective specimen scores. The network computing entity 20 provides the respective specimen scores via a scoring response, for example.

At step/operation 608, the user computing entity 30 receives the scoring response. For example, the user computing entity receives (e.g., via network interface 320, receiver 306, and/or the like) a scoring response provided in response to the specimen scoring request or by accessing a specimen score database stored by the network computing entity 20.

At step/operation 610, the user computing entity 30 processes the specimen response to generate respective graphical representations of one or more specimen scores provided by the specimen response. In an example embodiment, the graphical representation of a specimen score is a numerical, alphanumerical, color-coded and/or other human discernable indication of the predicted probability of a successful outcome corresponding to a respective specimen. For example, the graphical representation of the specimen scores may be a table providing a percentage indicating the predicted probability of a successful outcome corresponding to a respective specimen and an indication of which holding location of the slide 10 at which the respective specimen is located. In another example, the graphical representation may include an illustration of the slide 10 with holding locations of the slide 10 color-coded to indicate the predicted probability of a successful outcome corresponding to a respective specimen located at a respective holding location of the slide 10. Various formats for providing a graphical representation of the specimen score(s) are utilized in various embodiments.

At step/operation 612, the user computing entity 30 causes display of the graphical representation of the specimen scores (e.g., via display 316). For example, the user computing entity 30 (e.g., processing device 308) may render the graphical representation of the specimen scores and cause the display 316 to display the graphical representation of the specimen scores.

A technician or medical service provider operating the user computing entity 30 may determine, based on the graphical representation of the specimen scores, which specimen to select for use in a fertilization event. For example, the technician or medical service provider may select a sperm for use in performing the fertilization event based on the graphical representation of the specimen scores, retrieve the selected sperm from a respective location of the slide 10, and use the sperm to perform the fertilization event. An outcome of the fertilization event may be stored in association with imaging data corresponding to the selected sperm such that the information corresponding to the selected sperm may be used to further train the specimen analysis model in the future. Thus, the specimen score enables the technician or medical service provider to select sperm that are likely to provide successful outcomes for fertilization events.

Technical Advantages

As described in detail elsewhere herein, a technical problem exists regarding how to effectively identify sperm that are likely to achieve successful fertilization, healthy embryo development, and/or a successful live birth outcome when the specimen is used to perform a fertilization event without rendering the individual sperm unusable. For example, conventional techniques either do not appear to provide any significant advantage over manual sperm selection techniques or render the individual sperm unusable.

Various embodiments disclosed herein provide technical solutions to these technical problems. In particular, various embodiments use specimen image data corresponding to at least one of vibrational microspectroscopy or quantitative phase imaging (QPI). For example, specimen imaging data of one or more specimen is captured using at least one of vibrational microspectroscopy or QPI techniques. These imaging techniques do not damage the specimen but provide sufficient information for the specimen analysis model to differentiate between individual specimen that are likely to result in successful outcomes versus individual specimen that are less likely or not likely to result in successful outcomes when used to perform a fertilization event. Thus, various embodiments provide specimen scores that provide for improved outcomes of fertilization events when sperm are selected for performance of the fertilization events using the specimen scores compared to conventional methods. Moreover, the specimen imaging data capturing process(es) and the specimen score determination and provision time frame do not render the individual specimen unusable. Thus, the specimen scores can be used to directly select individual specimen in real time (or near real time) for performance of fertilization events. Thus, various embodiments provide improvements to the technical fields of sperm analysis and selection of sperm for performing fertilization events.

V. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:

obtaining, by a user computing entity, respective specimen data comprising imaging data, the imaging data comprising at least one of respective Raman microspectroscopy data or respective quantitative phase imaging (QPI) data for each individual specimen of one or more specimen, the imaging data for each individual specimen of the one or more specimen captured via non-invasive imaging of the individual specimen, wherein the imaging data is captured of the one or more specimen with the one or more specimen contained within a slide that spatially isolates individual specimen of the one or more specimen, and wherein the respective specimen data is associated with sample data that provides at least one of demographic information or medical history information of a source of the individual specimen;

generating, by the user computing entity, a specimen scoring request comprising at least a portion of the respective specimen data;

providing, by the user computing entity, the specimen scoring request for receipt by at least one network computing entity;

receiving, by the user computing entity, a specimen response comprising a respective specimen score for each of the one or more specimen, the respective specimen score for each of the one or more specimen generated by a machine-learning trained specimen analysis model executed by the at least one network computing entity and trained to receive a representation of the imaging data comprising the at least one of respective Raman micro-spectroscopy data or respective QPI data and a representation of the sample data as input and, as output, provide a prediction of a fertilization event outcome for the individual specimen, the prediction determined based at least in part on DNA characteristics of the individual specimen ascertained from at least one the representation of the imaging data or the representation of the sample data, the specimen response provided by the at least one network computing entity;

processing, by the user computing entity, the respective specimen score for at least one of the one or more specimen to generate a graphical representation of the respective specimen score; and causing, by the user computing entity, display of the graphical representation of the respective specimen score.

2. The method of claim 1, wherein the respective specimen score provides an outcome prediction for an assisted reproductive technology process performed using the respective specimen of the one or more specimen and the respective specimen is usable for a fertilization event.

3. The method of claim 1, further comprising receiving the sample data providing source information for the one or more specimen, wherein the specimen scoring request comprises the sample data and the specimen score is generated by the machine-learning trained specimen analysis model based at least in part on the sample data.

4. The method of claim 1, wherein the machine-learning trained specimen analysis model is configured to analyze a feature vector corresponding to the respective specimen of the one or more specimen and generated based at least in part on the imaging data of the respective specimen.

5. The method of claim 1, wherein the machine-learning trained specimen analysis model was trained using a self-supervised machine learning technique and each of the one or more specimen is an individual sperm.

6. The method of claim 1, wherein the respective specimen data comprises imaging data corresponding to both vibrational microspectroscopy and quantitative phase imaging.

7. The method of claim 1, wherein the specimen analysis model is trained to determine a probability that the individual specimen includes a particular sex chromosome.

8. The method of claim 1, wherein the machine-learning trained specimen analysis model was trained based on training image data labeled with information corresponding to at least one of successful fertilization, embryo development, or live birth out comes of a corresponding specimen shown in the training image data.

9. The method of claim 1, wherein the one or more specimen are held in isolation in the respective wells of the slide while the user computing entity obtains the respective specimen data, generates the specimen scoring request, provides the specimen scoring request, receives the specimen response, processes the respective specimen score, and causes display of the graphical representation of the respective specimen score.

10. The method of claim 1, wherein a phase map is generated based on the respective QPI data and provided as input to the machine-learning trained specimen analysis model as at least part of a two-dimensional or three-dimensional feature vector determined based at least in part on the specimen data.

11. A user computing entity comprising at least one processor and a memory storing computer-executable instructions, the computer-executable instructions configured to, when executed by the at least one processor, cause the user computing entity to perform the steps of:
obtaining respective specimen data comprising imaging data, the imaging data comprising at least one of respective Raman micro-spectroscopy data or respective quantitative phase imaging (QPI) data for each individual specimen of one or more specimen, the imaging data for each individual specimen of the one or more specimen captured via non-invasive imaging of the individual specimen, wherein the imaging data is captured of the one or more specimen with the one or more specimen contained within a slide that spatially isolates individual specimen of the one or more specimen, and wherein the respective specimen data is associated with sample data that provides at least one of demographic information or medical history information of a source of the individual specimen;
generating a specimen scoring request comprising at least a portion of the respective specimen data;
providing the specimen scoring request for receipt by at least one network computing entity;
receiving a specimen response comprising a respective specimen score for each of the one or more specimen, the respective specimen score for each of the one or more specimen generated by a machine-learning trained specimen analysis model executed by the at least one network computing entity and trained to receive a representation of the imaging data comprising the at least one of respective Raman micro-spectroscopy data or respective QPI data and a representation of the sample data as input and, as output, provide a prediction of a predict fertilization event outcome for the individual specimen, the prediction determined based at least in part on DNA characteristics of the individual specimen ascertained from at least one the representation of the imaging data or the representation of the sample data, the specimen response provided by the at least one network computing entity;
processing the respective specimen score for at least one of the one or more specimen to generate a graphical representation of the respective specimen score; and
causing display of the graphical representation of the respective specimen score.

12. The user computing entity of claim 11, wherein the respective specimen score provides an outcome prediction for an assisted reproductive technology process performed using the respective specimen of the one or more specimen and the respective specimen is usable for a fertilization event.

13. The user computing entity of claim 11, wherein the computer-executable instructions are further configured to, when executed by the at least one processor, cause the user computing entity to perform the steps of receiving the sample data providing source information for the one or more specimen, wherein the specimen scoring request comprises the sample data and the specimen score is generated by the machine-learning trained specimen analysis model based at least in part on the sample data.

14. The user computing entity of claim 11, wherein the machine-learning trained specimen analysis model is configured to analyze a feature vector corresponding to an individual specimen of the one or more specimen and generated based at least in part on the Raman micro-spectroscopy data of the respective specimen.

15. The user computing entity of claim 11, wherein the machine-learning trained specimen analysis model was trained using a self-supervised machine learning technique.

16. The user computing entity of claim 11, wherein each of the one or more specimen is an individual sperm.

17. The user computing entity of claim 11, wherein the machine-learning trained specimen analysis model was trained based on training image data labeled with information corresponding to at least one of successful fertilization, embryo development, or live birth out comes of a corresponding specimen shown in the training image data.

18. A network computing entity comprising at least one processor and a memory storing computer-executable instructions, the memory and the computer-executable instructions configured, when executed by the at least one processor, to cause the network computing entity to:
receive specimen data, wherein the specimen data comprises specimen imaging data comprising at least one of a representation of respective Raman micro-spectroscopy data or a representation of respective quantitative phase imaging (QPI) data for each individual specimen of one or more specimen, the imaging data for a respective specimen of the one or more specimen captured via non-invasive imaging of the respective specimen, wherein the one or more specimen are held in isolation in respective wells of a slide while the imaging data is captured, and wherein the specimen data is associated with sample data that provides at least one of demographic information or medical history information of a source of the individual specimen;
execute a machine-learning trained specimen analysis model to process at least a portion of the specimen imaging data and the sample data to generate a respective specimen score for at least one of the one or more specimen, wherein the machine-learning trained specimen analysis model has been trained to predict fertilization event outcomes for individual specimen based at least in part on DNA characteristics of the individual specimen determined based at least in part on the at least one of the representation of respective Raman micro-spectroscopy data or the representation of QPI data and the sample data; and
provide a specimen response comprising the respective specimen score for receipt by a user computing entity.

19. The network computing entity of claim 18, wherein the memory and the computer-executable instructions are further configured, when executed by the at least one processor, to cause the network computing entity to, prior to generating the respective specimen score, train the machine-learning trained specimen analysis model by training a specimen analysis model, the specimen analysis model trained using a plurality of training imaging data instances where each training imaging data instance (a) comprises at least one of vibrational microspectroscopy data or QPI data for a single sperm and (b) is labelled with an outcome of a fertilization event including the single sperm.

20. The network computing entity of claim 18, wherein the memory and the computer-executable instructions are further configured, when executed by the at least one processor, to cause the network computing entity to, prior to generating the respective specimen score, train the machine-learning trained specimen analysis model by:
- pre-training the specimen analysis model using initial training data comprising at least one collected training data instances or generated training data instances;
- identifying additional training data instances, the additional training data instances comprising imaging data representing one or more morphological features of specimen indicated by a notification generated responsive to the pre-training of the specimen analysis model; and
- further training the specimen analysis model using the additional training data instances.

* * * * *

UNITED STATES PATENT AND TRADEMARK OFFICE
CERTIFICATE OF CORRECTION

| | | |
|---|---|---|
| PATENT NO. | : 12,094,570 B2 | Page 1 of 1 |
| APPLICATION NO. | : 18/048564 | |
| DATED | : September 17, 2024 | |
| INVENTOR(S) | : Epstein | |

It is certified that error appears in the above-identified patent and that said Letters Patent is hereby corrected as shown below:

In the Claims

<u>Column 33,</u>
Line 58, Claim 11, "a predict fertilization" should read --a fertilization--.

Signed and Sealed this
Sixth Day of May, 2025

Coke Morgan Stewart
*Acting Director of the United States Patent and Trademark Office*